United States Patent
Chu et al.

(10) Patent No.: US 6,979,322 B2
(45) Date of Patent: Dec. 27, 2005

(54) LOW PROFILE ADAPTOR FOR USE WITH A MEDICAL CATHETER

(75) Inventors: Michael S. H. Chu, Brookline, MA (US); Laddvanh Bouphavichith, Clinton, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 468 days.

(21) Appl. No.: 10/037,807

(22) Filed: Dec. 26, 2001

(65) Prior Publication Data

US 2003/0120260 A1    Jun. 26, 2003

(51) Int. Cl.[7] ................. A61M 5/00; A61M 25/16
(52) U.S. Cl. ....................... 604/248; 604/533
(58) Field of Search ............... 604/248, 533, 604/245, 246, 247, 256, 260, 174, 175

(56) References Cited

U.S. PATENT DOCUMENTS

| | | |
|---|---|---|
| 3,926,187 A | 12/1975 | Iglesias |
| 4,306,545 A | 12/1981 | Ivan et al. |
| 4,390,017 A | 6/1983 | Harrison et al. |
| 4,417,890 A | 11/1983 | Dennehey et al. |
| 4,424,833 A | 1/1984 | Spector et al. |
| 4,473,369 A | 9/1984 | Lueders et al. |
| 4,557,261 A | 12/1985 | Rügheimer |
| 4,603,837 A * | 8/1986 | Steer ............ 251/352 |
| 4,774,944 A | 10/1988 | Mischinski |
| 4,826,477 A | 5/1989 | Adams |
| 4,834,712 A | 5/1989 | Quinn et al. |
| 4,863,438 A | 9/1989 | Gauderer et al. |
| 4,944,732 A | 7/1990 | Russo |
| 5,007,900 A | 4/1991 | Picha et al. |
| 5,026,352 A | 6/1991 | Anderson |

(Continued)

FOREIGN PATENT DOCUMENTS

DE    3314640    11/1983

(Continued)

OTHER PUBLICATIONS

International Search Report for PCT Application No. PCT/EP/14754, (the corresponding PCT application to the present application), mailed May 8, 2003.

*Primary Examiner*—Sharon Kennedy
(74) *Attorney, Agent, or Firm*—Kriegsman & Kriegsman

(57) ABSTRACT

Low profile adaptor for use with a medical catheter, such as a gastrostomy feeding tube. In a preferred embodiment, the adaptor comprises a body having a lower portion and an upper portion. A first channel is provided in the lower portion, and a second channel is provided in the upper portion, the first and second channels being perpendicular to and in fluid communication with one another. A generally cylindrical stem is coaxially positioned within the second channel, the stem being rotatably mounted about its longitudinal axis. The stem is hollow and has an open front end, a closed rear end and a hole in its side wall, the hole being rotatably alignable with the first channel. To facilitate rotational alignment of the hole with the first channel, a stop is formed on the exterior of the stem, the stop being engageable with a surface positioned within the second channel. The front end of the stem is recessed relative to the front end of the second channel to prevent unwanted rotation of the stem. Rotation of the stem from a closed position to an open position is achieved by screwing a syringe onto the front end of the stem. The proximal end of the gastrostomy feeding tube is inserted over the lower portion of the body and is secured thereto with a nut.

31 Claims, 9 Drawing Sheets

U.S. PATENT DOCUMENTS

| | | |
|---|---|---|
| 5,071,405 A | 12/1991 | Piontek et al. |
| 5,100,394 A | 3/1992 | Dudar et al. |
| 5,112,310 A | 5/1992 | Grobe |
| 5,158,569 A | 10/1992 | Strickland et al. |
| 5,167,627 A | 12/1992 | Clegg et al. |
| 5,169,385 A * | 12/1992 | Turnbull ............... 604/32 |
| 5,259,399 A | 11/1993 | Brown |
| 5,267,983 A | 12/1993 | Oilschlager et al. |
| 5,290,250 A | 3/1994 | Bommarito |
| 5,358,488 A | 10/1994 | Surlyapa |
| 5,488,949 A | 2/1996 | Kreifels et al. |
| 5,549,657 A | 8/1996 | Stern et al. |
| 5,720,734 A | 2/1998 | Copenhaver et al. |
| 5,836,924 A | 11/1998 | Kelliher et al. |
| 5,947,954 A * | 9/1999 | Bonaldo ............... 604/533 |
| 6,019,746 A | 2/2000 | Picha et al. |
| 6,095,997 A | 8/2000 | French et al. |
| 6,419,699 B1 | 7/2002 | Schuessler |
| 6,569,145 B1 * | 5/2003 | Shmulewitz et al. ....... 604/509 |
| 2002/0022801 A1 | 2/2002 | DeLegge |

FOREIGN PATENT DOCUMENTS

| | | |
|---|---|---|
| EP | 976 418 | 2/2000 |
| WO | WO 02/13901 A1 | 2/2002 |

* cited by examiner

LOW PROFILE ADAPTOR FOR USE WITH A MEDICAL CATHETER

BACKGROUND OF THE INVENTION

The present invention relates generally to medical catheters, such as gastrostomy feeding tubes, and relates more particularly to low profile adaptors well-suited for use with medical catheters.

Certain patients are unable to take food transorally due to an inability to swallow. Such an inability to swallow may be due to a variety of reasons, such as esophageal cancer, neurological impairment and the like. Although the intravenous administration of food to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. Feeding is then typically performed by administering food through a feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy. In one type of percutaneous endoscopic gastrostomy (PEG) technique, the distal end of an endoscope is inserted into a patient's mouth and is passed through the esophagus into the stomach. After distension of the stomach by inflation, an entry site on the abdomen is identified and an incision can be made. A needle, with an outer cannula, is inserted through the entry site across the abdominal and gastric walls. While keeping the cannula in place, the needle is then removed and a flexible wire is passed through the cannula into the stomach. A snare loop is extended from the distal end of the endoscope. The endoscopic snare loop is then used to grasp the wire, the cannula is released, and the endoscope and wire are withdrawn through the esophagus and mouth of the patient. A silicone gastrostomy feeding tube, the distal end of which is attached to a silicone, dome-shaped internal bolster, is then secured to the wire and is pulled from its proximal end through the esophagus and into the stomach until the internal bolster engages the stomach wall and the feeding tube extends through the stomach and abdominal walls, with the proximal end of the feeding tube extending approximately one foot beyond the abdominal wall. (Over a period of several days following implantation of the feeding tube, a stable stoma tract forms around the feeding tube between the gastric and abdominal walls.)

With the internal bolster in place against the gastric wall, an external bolster is typically secured to the feeding tube to engage the abdomen so as to prevent longitudinal movement of the feeding tube within the stoma tract. Additionally, a "Y-port" adapter is typically attached to the proximal end of the feeding tube, the Y-port adapter being adapted to receive a pair of connector tips through which food and/or medications may be dispensed. In addition, a detachable locking clip is typically secured to the feeding tube at a point between the external bolster and the Y-port adapter to prevent gastric fluids from escaping through the proximal end of the feeding tube when the feeding tube is not in use.

Alternative techniques for implanting gastrostomy feeding tubes using percutaneous endoscopic gastrostomy are disclosed in U.S. Pat. No. 5,112,310, inventor Grobe, which issued May 12, 1992, and U.S. Pat. No. 5,167,627, inventors Clegg et al., which issued Dec. 1, 1992, both of which are incorporated herein by reference.

Although gastrostomy feeding tubes of the type described above work well for their intended purpose, many active patients find the nearly one foot length of tubing that extends externally to be unwieldy, difficult to conceal and susceptible to being inadvertently pulled on. As can readily be appreciated, these conditions are potential sources of physical and/or psychological trauma to the patient. Consequently, a variety of low-profile replacement tube assemblies (also referred to in the art as low-profile replacement PEG devices) have been designed for implantation within the stoma tract following the removal of an initially-implanted gastrostomy feeding tube. Such replacement assemblies are referred to as being "low-profile" because they are considerably more compact externally than the above-described initially-implanted gastrostomy feeding tube assemblies.

An example of a low-profile replacement PEG device is disclosed in U.S. Pat. No. 4,944,732, inventor Russo, which issued Jul. 31, 1990, and which is incorporated herein by reference. The low-profile replacement PEG device of said patent comprises a deformable, conical tip portion having at least one side aperture therethrough, a tube portion which extends rearwardly from the tip portion, a fitting portion on the rear end of the tube portion, a removable valve portion in the fitting portion and a flange portion which extends outwardly from the fitting portion. The device is adapted to be installed in a patient so that the tube portion extends through a pre-established stoma with the tip portion located in the patient's stomach and with the fitting portion and the flange portion engaging the skin of the patient adjacent the stoma.

The deformable tip portion of the above-described low-profile replacement PEG device functions as an internal bolster to anchor its associated tube portion in a patient's stomach. To implant and/or remove the aforementioned tube portion from a patient's stomach, an obturator or similar device is typically inserted through the tube portion and is used to elongate or otherwise deform the tip portion in such a way as to permit the tip portion to fit through the stoma. Removal of the obturator from the tip portion then permits the tip portion to expand to its original shape for anchoring.

Another type of low-profile replacement PEG device uses an inflatable balloon, instead of a deformable tip portion, as an internal bolster to retain the distal end of its associated tube within a patient's stomach. To implant such a device in a patient, the inflatable balloon is deflated, the distal end of the tube portion is inserted through the stoma, and the balloon is then inflated. To remove the implanted device from a patient, the balloon is deflated and the tube is then withdrawn from the stoma.

Further examples of low-profile replacement PEG devices are disclosed in U.S. Pat. No. 4,863,438, inventors Gauderer et al., which issued Sep. 5, 1989; and U.S. Pat. No. 5,720,734, inventors Copenhaver et al., which issued Feb. 24, 1998, both of which are incorporated herein by reference.

Although low-profile replacement PEG devices are less awkward and bulky than initially-implanted gastrostomy tube assemblies, the use of such low-profile replacement PEG devices suffers from its own set of shortcomings. One such shortcoming is that the implantation of a low-profile replacement PEG device must be preceded by the removal of an initially-implanted gastrostomy tube. Such removal typically involves pulling on the proximal end of the gastrostomy tube until the internal bolster fails and is drawn through the stoma. As can readily be appreciated, such a procedure can be quite painful to the patient and can result in damage to the stoma, thereby delaying when the replacement device can be implanted.

Another shortcoming of many low-profile replacement PEG devices is that such devices typically do not last as long as initially-implanted gastrostomy tube assemblies (most commonly due to failure of their internal anchoring mechanisms or due to clogging or other failure of their valve mechanisms) and, therefore, must be replaced more frequently than is the case with initially-implanted gastrostomy tube assemblies.

Still another shortcoming of many low-profile replacement PEG devices is that such devices are typically not adjustable in length. This can be problematic because there is often an appreciable variation in stoma length from patient to patient. Consequently, it is typically necessary, after removal of the initially-implanted tube and prior to implantation of the replacement device, to measure the length of the stoma and then to select a replacement device having an appropriate length. As can readily be appreciated, this approach requires that there be made available an inventory of replacement devices of varying lengths.

In order to avoid the aforementioned shortcomings of low-profile replacement PEG devices while, at the same time, avoiding the above-described problems associated with having a gastrostomy tube extend externally for a substantial length, there have recently been devised a number of adaptors designed for use in converting an initially-implanted gastrostomy tube into a low-profile PEG device. One such adaptor is disclosed in U.S. Pat. No. 5,549,657, inventors Stern et al., which issued Aug. 27, 1996, and which is incorporated herein by reference. According to said patent, an adaptor is disclosed therein that is designed for use with a gastostomy feeding tube which has been inserted by means of conventional endsocopic procedures and which has been cut to a desired length by a surgeon. The adaptor is said to comprise an anti-reflux valve assembly having a stem which can be plugged into the open end of the feeding tube. The valve assembly is said to contain a seal which functions as a one-way valve to prevent reflux of gastric contents but which permits the introduction of feeding solution into the feeding tube. A clamp is placed around the feeding tube and the valve stem and is locked into place to secure the valve assembly to the feeding tube at a location flush with the patient's skin. A silicone cover is placed around the clamp to protect the patient from skin irritation caused by the clamp and also to protect the clamp and valve assembly from contaminants.

Although the aforementioned adaptor favorably addresses some of the problems discussed above, the present inventors have identified certain shortcomings associated therewith. One such shortcoming is that the valve assembly of the subject adaptor relies upon the use of a silicone gasket having a Y-shaped slot through which a cannula is typically inserted to deliver food and/or medications. However, such a silicone gasket, after repeated insertions of the cannula therethrough, has a tendency to tear or to otherwise fail to act reliably as a one-way valve. Consequently, because the adaptor cannot easily be disconnected from the gastrostomy feeding tube once connected thereto, replacement of a worn adaptor requires the removal and replacement of the gastrostomy tube as well.

Another shortcoming with the aforementioned adaptor is that it possesses a relatively small lumen through which fluid may pass. In addition, due to its manner of operation, the valve tends to get clogged over time, further restricting fluid flow.

Still another shortcoming with the aforementioned adaptor is that the clamp of said adaptor has a tendency to pinch the proximal end of the gastrostomy tube at those points where the male and female sections of the clamp are joined. Such pinching, over time, has a tendency to cause the tube to tear.

SUMMARY OF THE INVENTION

It is an object of the present invention to provide a novel low profile adaptor designed for use with a medical catheter, such as a gastrostomy feeding tube.

It is another object of the present invention to provide a low profile adaptor as described above which, when used with a gastrostomy feeding tube, overcomes at least some of the shortcomings discussed herein in connection with PEG devices, in general, and low profile PEG adaptors, in particular.

Therefore, according to one aspect of the invention, there is provided an adaptor well-suited for use with a medical catheter, such as a gastrostomy feeding tube, said adaptor comprising (a) a lumen, said lumen being adapted for fluid communication with the medical catheter; and (b) a tube, said tube being adapted for fluid communication with an external conduit, said tube being rotatable about its longitudinal axis between an open position in which said tube is in fluid communication with said lumen and a closed position in which said tube is not in fluid communication with said lumen.

According to another aspect of the invention, there is provided an adaptor well-suited for use with a medical catheter, such as gastrostomy feeding tube, said adaptor comprising (a) a body, said body being provided with a first channel and a second channel, said first channel and said second channel being in fluid communication with one another, said first channel being adapted for fluid communication with a medical catheter; and (b) a stem, said stem having a front end, a rear end, a side wall, a cavity extending rearwardly from said front end, and a hole in said side wall in fluid communication with said cavity, said stem being mounted within said second channel of said body and being rotatable between an open position in which said stem and said first channel are in fluid communication with one another via said hole and a closed position in which said stem and said first channel are not in fluid communication with one another.

In a preferred embodiment, the adaptor comprises a body having a lower portion and an upper portion. A first channel is provided in the lower portion, and a second channel is provided in the upper portion, the first and second channels being perpendicular to and in fluid communication with one another. A generally cylindrical stem is coaxially positioned within the second channel, the stem being rotatably mounted about its longitudinal axis. The stem is hollow and has an open front end, a closed rear end and a hole in its side wall, the hole being rotatably alignable with the first channel. To facilitate rotational alignment of the hole with the first channel, a stop is formed on the exterior of the stem, the stop being engageable with a surface positioned within the second channel. The front end of the stem is recessed relative to the front end of the second channel to prevent unwanted rotation of the stem. An external thread is formed on the front end of the stem. Rotation of the stem from a closed position to an open position is achieved by screwing onto the front end of the stem an internally threaded member that matingly engages the external thread on the front end of the stem. The proximal end of the gastrostomy feeding tube is inserted over the lower portion of the body and is secured thereto with a nut.

As can readily be appreciated, although the adaptors discussed above are described as being low profile adaptors, such adaptors are also suitable for use with medical catheters, such as gastrostomy feeding tubes, that extend externally for several inches. Accordingly, the adaptors of the present invention are not limited to being low profile adaptors.

The present invention is also directed to a PEG device comprising a gastrostomy feeding tube having a proximal end and a distal end, an internal bolster secured to the distal end of the gastrostomy feeding tube, and an adaptor of the type described above secured to the proximal end of the gastrostomy feeding tube.

For purposes of the present specification and claims, relational terms like "top," "bottom," "upper," and "lower" are used to describe the present invention in a context in which the invention is secured to a catheter extending upwardly out of a patient. It is to be understood that, by orienting a patient such that the catheter extends outwardly in a direction other than upwardly, the corresponding description of the directionality of the invention will need to be adjusted accordingly.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference numerals represent like parts.

DETAILED DESCRIPTION OF PREFERRED EMBODIMENTS

Figure 1:
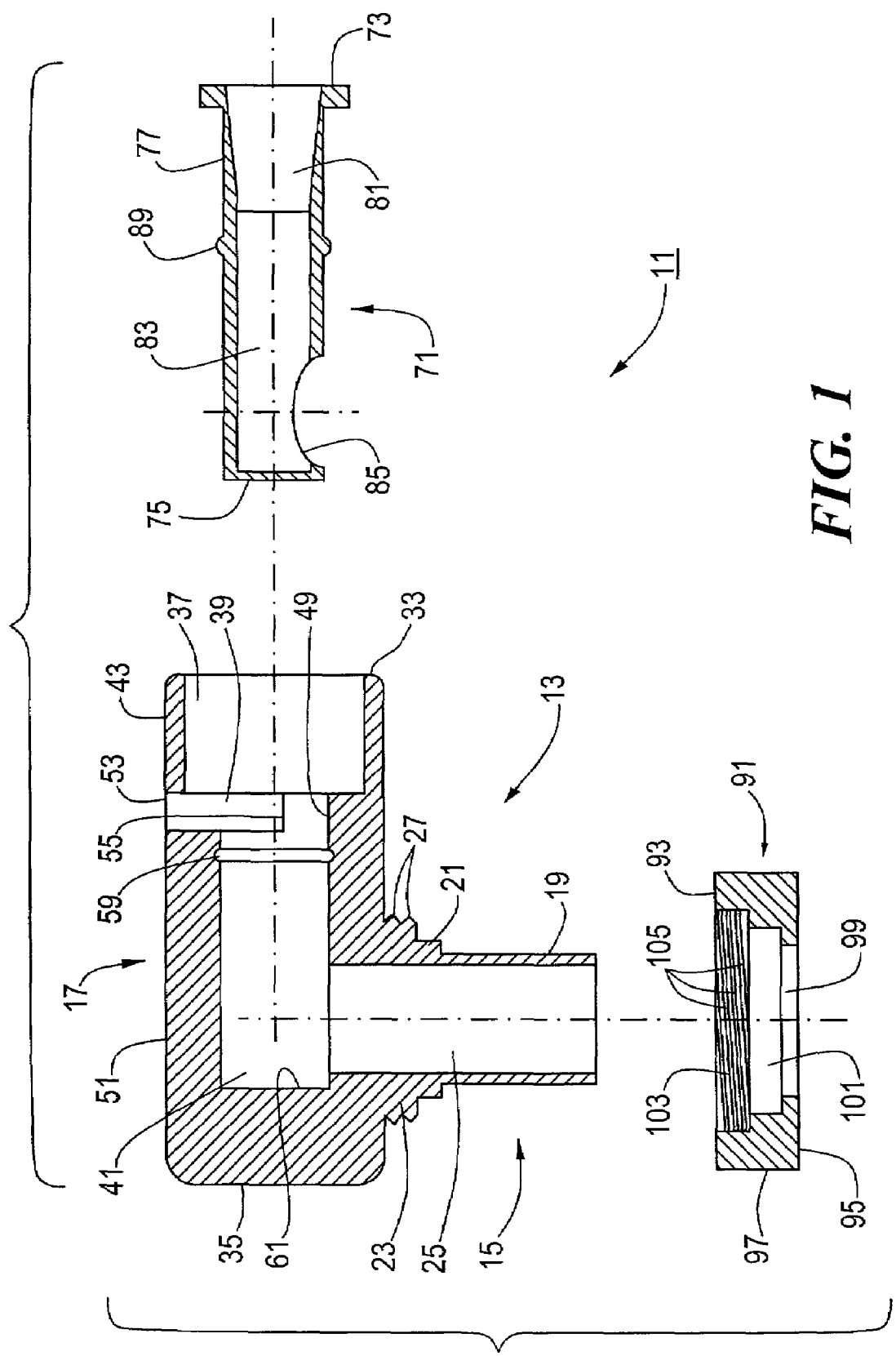
FIG. 1 is an exploded section view of a first embodiment of a low profile adaptor constructed according to the teachings of the present invention for use with a gastrostomy feeding tube.
Figure 2:
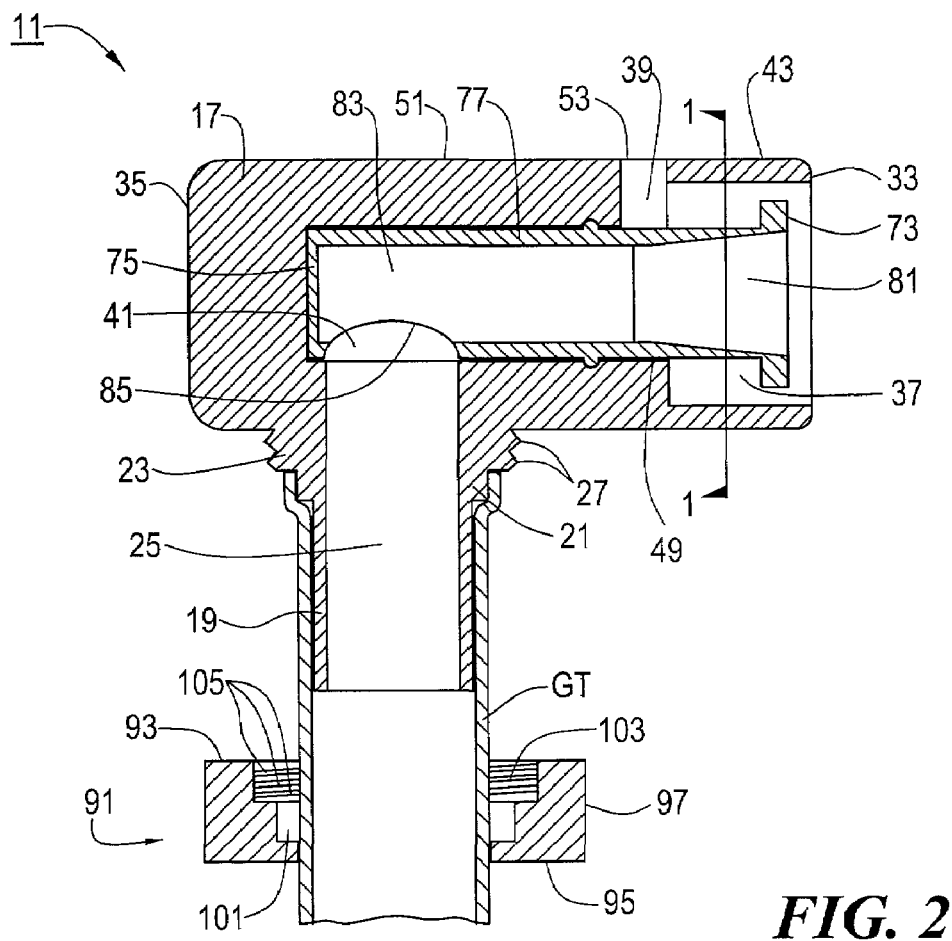
FIG. 2 is a partially exploded section view of the low profile adaptor of FIG. 1, said low profile adaptor being shown in its open position with a gastrostomy feeding tube inserted over a portion of the adaptor body.
Figure 3A:
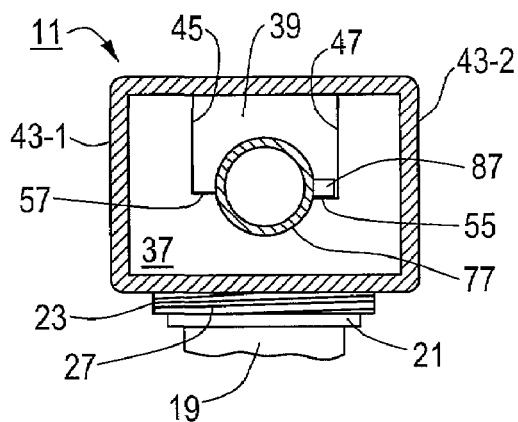
FIGS. 3(a) and 3(b) are fragmentary front section views of the low profile adaptor of FIG. 2 taken along line 1—1, said low profile adaptor being shown in its open and closed positions, respectively.
Figure 3B:
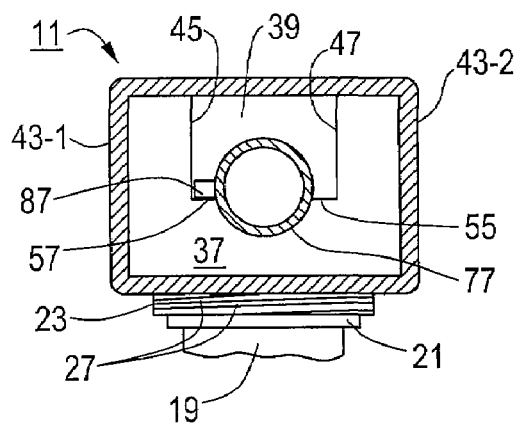
Figure 4A:
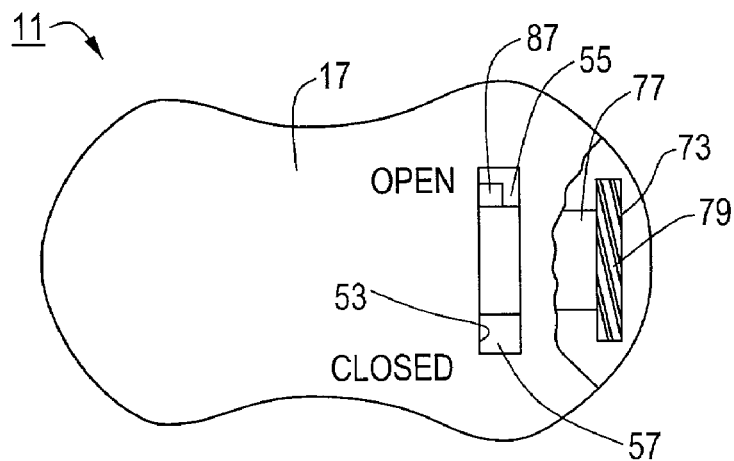
FIGS. 4(a) and 4(b) are top views, broken away in part, of the low profile adaptor of FIG. 1, said low profile adaptor being shown in its open and closed positions, respectively.
Figure 4B:
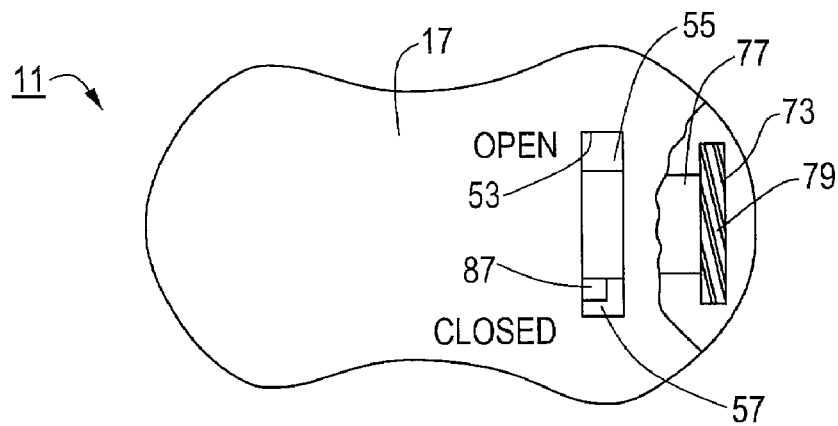

Referring now to FIGS. 1 through 5, there are shown various views of a first embodiment of a low profile adaptor constructed according to the teachings of the present invention for use with a medical catheter, such as a gastrostomy feeding tube, said low profile adaptor being represented generally by reference numeral 11.

Adaptor 11 comprises a body 13. Body 13, which is preferably made of molded medical grade plastic, is a unitary member shaped to include a lower portion 15 and an upper portion 17, lower portion 15 extending generally vertically and upper portion 17 extending generally horizontally and being positioned over lower portion 15.

Lower portion 15, which is generally cylindrical, is shaped to define a tube support 19 and a pair of steps 21 and 23 of increasing outer diameter at the top end of support 19. (Although two steps 21 and 23 are shown in the present embodiment, it can readily be appreciated that greater than or less than two steps could be formed at the top end of support 19.) A lumen 25 having a circular cross-section extends longitudinally through support 19 and steps 21 and 23 and continues for a short distance into upper portion 17 for reasons to become apparent below. As seen best in FIGS. 2 and 5, tube support 19 and step 21 are appropriately dimensioned so that a gastrostomy feeding tube GT may be inserted thereover. Also for reasons to become apparent below, step 23 is provided with external threads 27.

Upper portion 17, which, when viewed from above, has an hourglass shape to facilitate its being grasped with the thumb and forefinger of an operator, is provided with a channel that extends rearwardly from the front end 33 of upper portion 17 to a point prior to the rear end 35 of upper portion 17, said channel being shaped to include a front portion 37, an intermediate portion 39 and a rear portion 41. Front portion 37 is rectangular in transverse cross-section and is centered within front end 33 of upper portion 17 so that a rectangular shield 43 is formed bounding front portion 37 on all four sides thereof. Intermediate portion 39, which is smaller in overall transverse cross-sectional area than front portion 37, is equidistantly spaced between the left and right sides 43-1 and 43-2, respectively, of shield 43 and is shaped to define a left side 45, a right side 47, a bottom and an open top, said open top extending through the top 51 of upper portion 17 and serving as a window 53 for reasons to become apparent below. Said bottom of intermediate portion 39 is shaped to include a semi-circular groove 49 flanked on opposite sides by stop surfaces 55 and 57, the functions of groove 49 and stop surfaces 55 and 57 also to become apparent below. Rear portion 41 of the channel of upper portion 17 is generally cylindrical in shape, the bottom half of rear portion 41 being aligned with and sized to match groove 49. A groove 59 of increased transverse cross-sectional area is formed within rear portion 41 proximate to the front end thereof, the function of groove 59 to be discussed below. Rear portion 41 is in fluid communication with lumen 25 for reasons to become apparent below, with the rear end 61 of rear portion 41 extending just beyond lumen 25.

Figure 6:
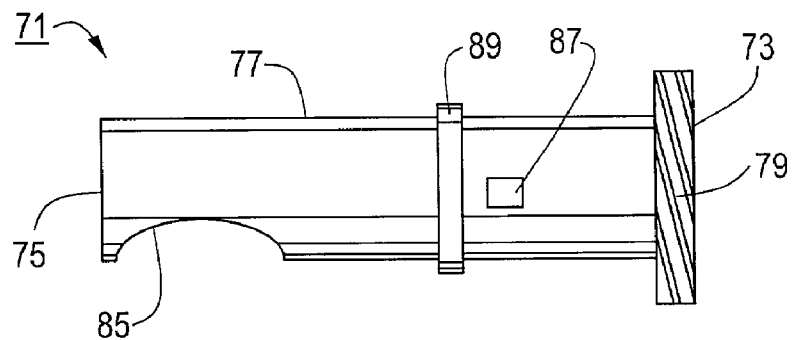
FIG. 6 is a side view of the stem shown in FIG. 1.

Adaptor 11 also comprises an elongated tube or stem 71 (shown separately in FIG. 6), stem 71 being rotatably mounted about its longitudinal axis within the aforementioned channel of upper portion 17. Stem 71, which is preferably made of molded medical grade plastic, is a generally cylindrical unitary member shaped to include a front end 73, a rear end 75 and a side wall 77. Stem 71 is sized so that front end 73 is spaced rearwardly relative to front end 33 of upper portion 17, with rear end 75 flush against rear end 61 of upper portion 17. Front end 73 is shaped to define a radially outwardly extending collar. Threads 79 are formed on the exterior perimeter of front end 73 for reasons to become apparent below. A channel is formed in stem 71, said channel comprising a front portion 81 and a rear portion 83. Front portion 81 extends rearwardly from front end 73 a short distance and is inwardly tapered from front end 73 to matingly receive a medical luer. Rear portion 83, which is generally cylindrical in shape, extends rearwardly from front portion 81 to a point just before rear end 75. A hole 85 is formed in side wall 77 for accessing rear portion 83, hole 85 being alignable, depending upon the rotational position of stem 71, with lumen 25. A stop block 87 is formed on the outside surface of side wall 77 for engaging stop surfaces 55 and 57, thereby delimiting the rotation of stem 71. An annular snap seal 89 is formed on the outside surface of side wall 77, snap seal 89 fitting into groove 59 so to keep stem 71 in place longitudinally within upper portion 17.

Adaptor 11 further comprises a ring-shaped member or nut 91, nut 91 serving as an external bolster for a gastrostomy feeding tube and being used to secure the gastrostomy feeding tube to body 13. Nut 91, which is preferably made of molded medical grade plastic, is a generally annular unitary member comprising a top surface 93, a bottom surface 95, an outer surface 97 and a central bore. The central bore is shaped to include a lower portion 99, an intermediate portion 101 and an upper portion 103. Lower portion 99 is appropriately dimensioned to securely receive tube support 19 and a gastrostomy feeding tube GT inserted thereover. Intermediate portion 101 is appropriately dimensioned to securely receive step 21 and the proximal end of the gastrostomy feeding tube GT. Upper portion 103 is appropriately dimensioned to securely receive step 23, upper portion 103 being provided with internal threads 105 for mating with external threads 27 of step 23.

Figure 5:
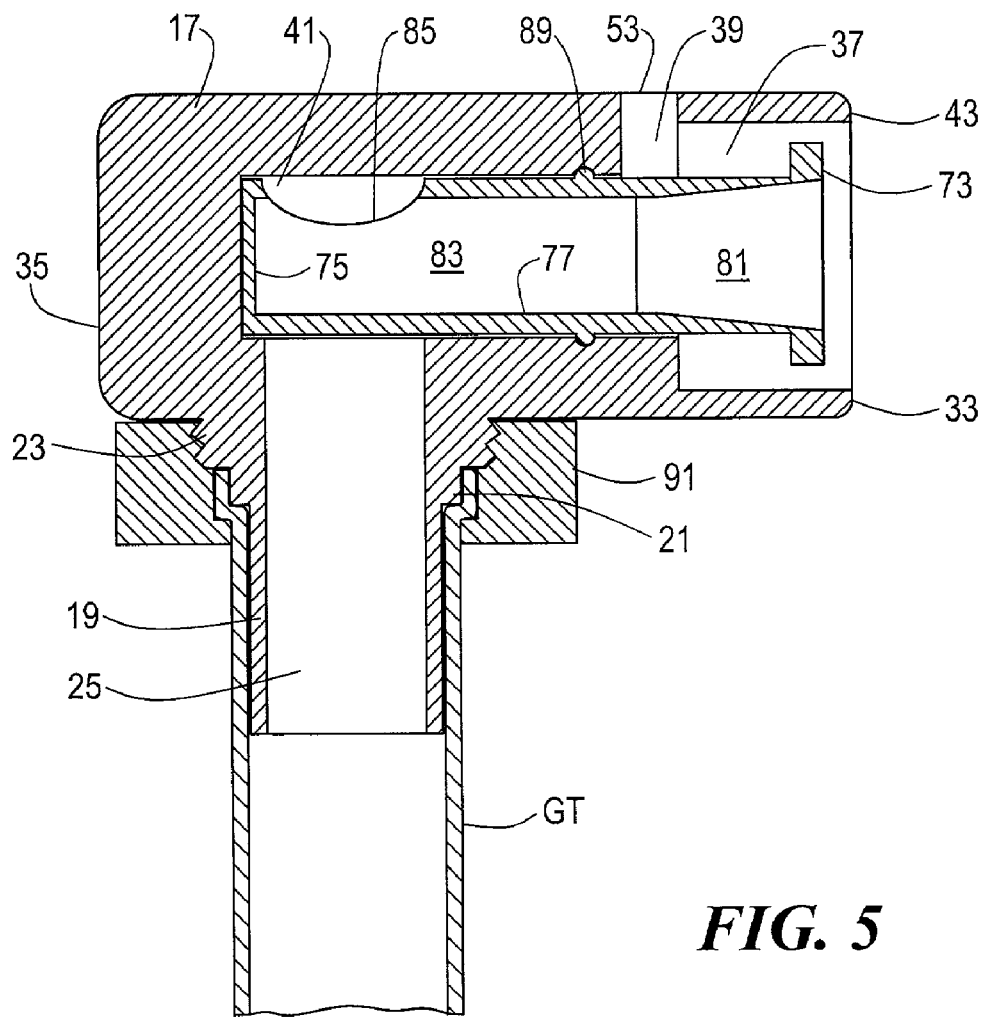
FIG. 5 is a section view of the low profile adaptor of FIG. 1, said low profile adaptor being shown in its closed position with a gastrostomy feeding tube securely connected thereto.

To convert a high profile gastrostomy feeding assembly to a low profile assembly using adaptor 11, a gastrostomy feeding tube is implanted in a patient by a physician in the manner described above so that the distal end of the tube is positioned in the patient's stomach and retained therein using an internal bolster, with the proximal end of the tube extending externally for a distance of several inches. The physician (or other medical care giver) then cuts the implanted gastrostomy feeding tube to a desired length. Nut 91 is then inserted over the proximal end of the gastrostomy feeding tube and is moved distally across the gastrostomy feeding tube until it is positioned against the patient's skin. With stem 71 preferably switched to its closed position within body 13, the physician then inserts the proximal end of the gastrostomy feeding tube GT up over tube support 19 and across step 21. Body 13 and the attached gastrostomy feeding tube are then lowered into nut 91, and step 23 is screwed into upper portion 103 of nut 91. Attachment of adaptor 11 to the gastrostomy feeding tube is now complete. As can be seen in FIG. 5, adaptor 11, in its closed state, serves to prevent reflux of gastric fluids conveyed by gastrostomy feeding tube GT.

Figure 7:
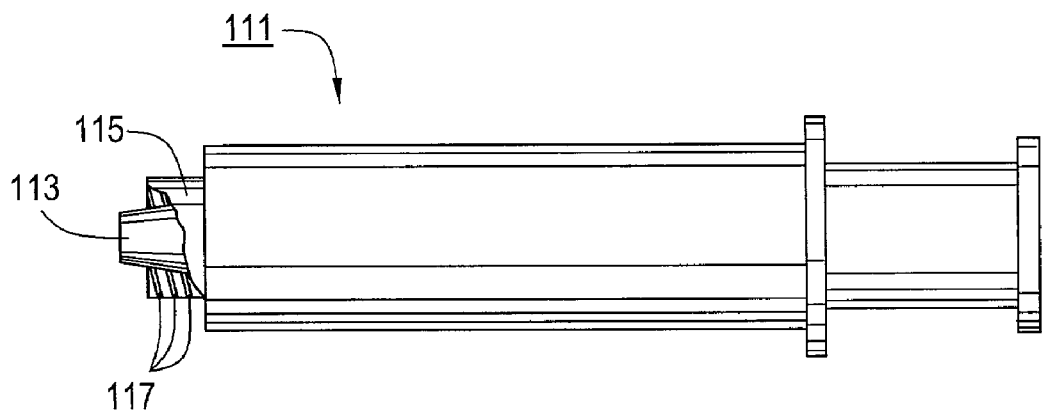
FIG. 7 is a side view, broken away in part, of a conventional syringe suitable for use with the adaptor of FIG. 1.

To deliver food and/or medications to a patient via adaptor 11, one may use a conventional syringe or tube of the type having at one end a medical luer surrounded by an internally threaded sleeve. An example of such a syringe is shown in FIG. 7, which depicts a syringe 111 having a front end shaped to include a medical luer 113 surrounded by a sleeve 115, sleeve 115 being provided with an internal thread 117. In use, luer 113 is inserted into front portion 81 of the channel of stem 71, and sleeve 115 is rotated clockwise. Initial rotation of sleeve 115 causes threads 117 to engage threads 79 of stem 71 and results in the rotation of stem 71 from its closed position wherein stop block 87 is positioned on top of stop surface 57 and hole 85 is turned approximately 180 degrees away from lumen 25 to its open position wherein stop block 87 is positioned on top of stop surface 55 and hole is aligned with lumen 25. (Stop block 87 is visible through window 53, and printed indicators on top 51 of upper portion 17 proximate to window 53 may be used to assist an operator in identifying whether stop block 87 is in an open or closed position.) Continued rotation of sleeve 115 will tighten the engagement of sleeve 115 to stem 71 but will not result in further rotation of stem 71 due to stop surface 55. With adaptor 11 now in its open position, food and/or medications may be dispensed from syringe 111 through adaptor 11. When the dispensing of food and/or medications is complete, sleeve 115 is rotated counterclockwise, causing stop block 87 to be moved from its open position on top of stop surface 55 to its closed position engaged with stop surface 57. Continued rotation of sleeve 115 will disengage sleeve 115 and luer 113 from stem 71, without further rotation of stem 71 due to stop surface 57.

As can be appreciated, one advantage of adaptor 11, as compared to existing valve-type adaptors of the type described above, is that its lumen size, in the open position, is not restricted. Another advantage is that adaptor 11 cannot easily be moved from a closed position to an open position, unless a device like syringe 111 is attached thereto. Still another advantage is that a device like syringe 111 cannot easily be pulled out of adaptor 11 when adaptor 11 is in its open position. Still yet another advantage is that adaptor 11, when in its open position, is connected to the delivery system in such a way as to prevent leakage of the fluids being administered to the patient and, when in its closed position, does not permit bodily fluids from the patient to escape therethrough.

As can also readily be appreciated, instead of being attached to a gastrostomy feeding tube, low-profile adaptor 11 could alternatively be attached to the proximal end of a jejunostomy feeding tube or could be used as a low-profile replacement enteral feeding device. Furthermore, in addition to being used for feeding, adaptor 11 could also be used for fluid drainage, for example, by being attached to a urine or blood drainage catheter.

As can further be appreciated, although body 13 is constructed in the present embodiment so that lumen 25 and the channel formed in upper portion 17 are perpendicular, one could adjust the angle therebetween, for example, enlarging the angle therebetween to facilitate alignment of a syringe with stem 71.

Figure 8:
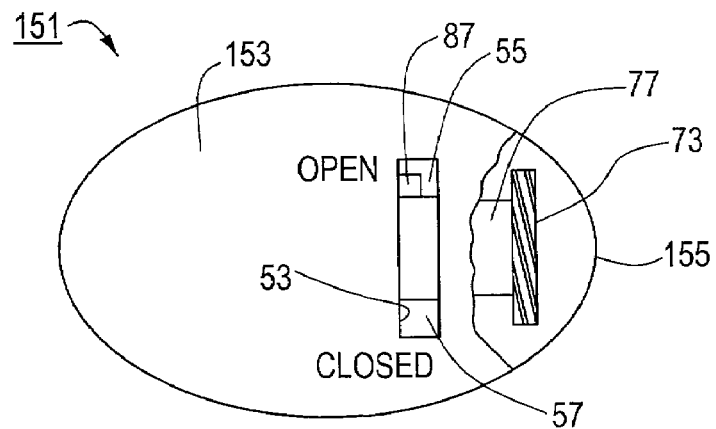
FIG. 8 is a top view, broken away in part, of a second embodiment of a low profile adaptor constructed according to the teachings of the present invention for use with a gastrostomy feeding tube, said low profile adaptor being shown in its open position.
Figure 9:
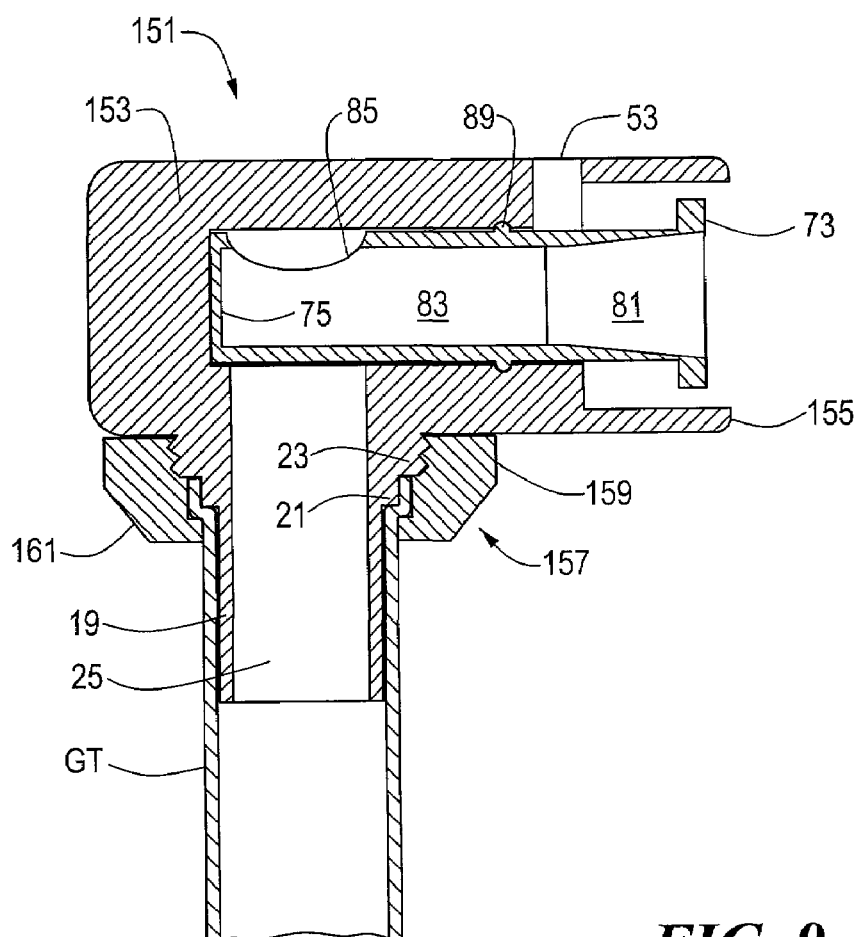
FIG. 9 is a section view of the low profile adaptor of FIG. 8, said low profile adaptor being shown in its closed position.

Referring now to FIGS. 8 and 9, there are shown top and section views of a second embodiment of a low profile adaptor constructed according to the teachings of the present invention for use with a medical catheter, such as a gastrostomy feeding tube, said low profile adaptor being represented generally by reference numeral 151.

Adaptor 151 is similar in most respects to adaptor 11, one difference between the two adaptors being that adaptor 151 comprises an upper portion 153 that, when viewed from above, is oval-shaped, as opposed to being hourglass-shaped. Another difference is that the front end 155 of upper portion 153 is shaped to shield stem 71 from the top and bottom, but not from the sides. Still another difference is that adaptor 151 comprises a nut 157 whose outer surface 159 includes a beveled region 161.

Figure 10:
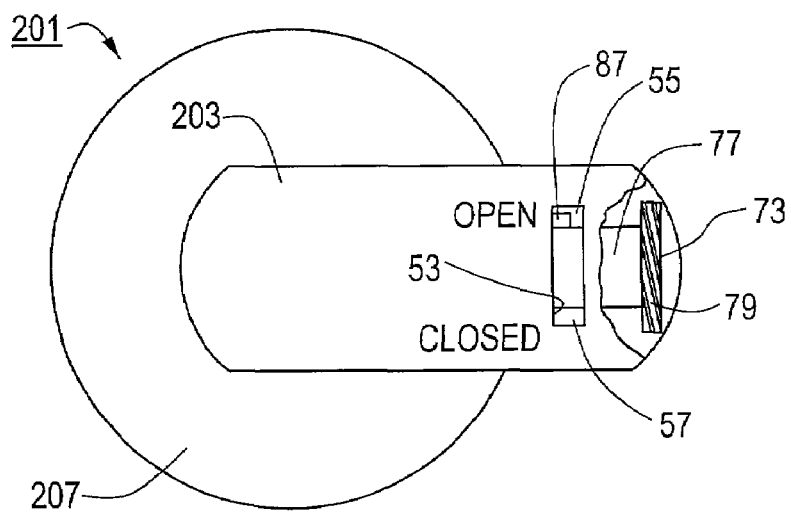
FIG. 10 is a top view, broken away in part, of a third embodiment of a low profile adaptor constructed according to the teachings of the present invention for use with a gastrostomy feeding tube, said low profile adaptor being shown in its open position.
Figure 11:
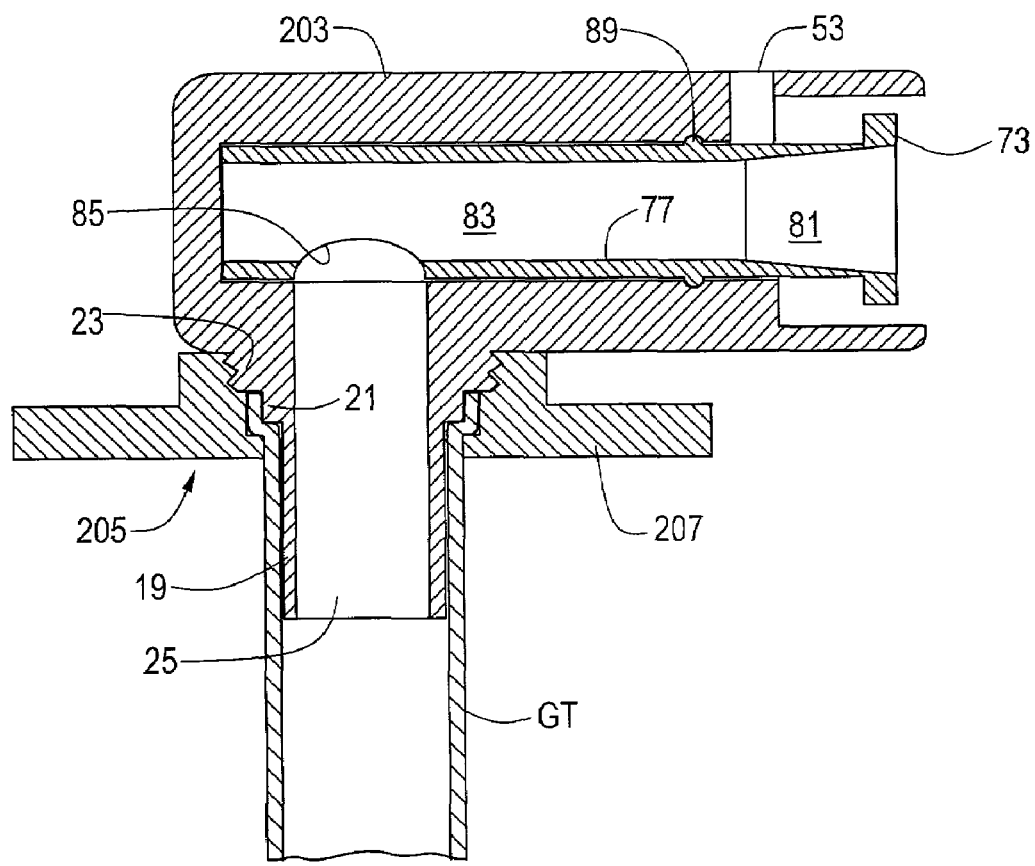
FIG. 11 is a section view of the low profile adaptor of FIG. 8, said low profile adaptor being shown in its open position.

Referring now to FIGS. 10 and 11, there are shown top and section views of a third embodiment of a low profile adaptor constructed according to the teachings of the present invention for use with a medical catheter, such as a gastrostomy feeding tube, said low profile adaptor being represented generally by reference numeral 201.

Adaptor 201 is similar in most respects to adaptor 11, one difference between the two adaptors being that adaptor 201 comprises an upper portion 203 that, when viewed from above, is generally rectangular with rounded ends, as opposed to being hourglass-shaped. Another difference is that adaptor 201 comprises a nut 205 having an outwardly extending flange 207. Still another difference is that adaptor 201 comprises a stem 209 having an open rear end 211.

Figure 12:
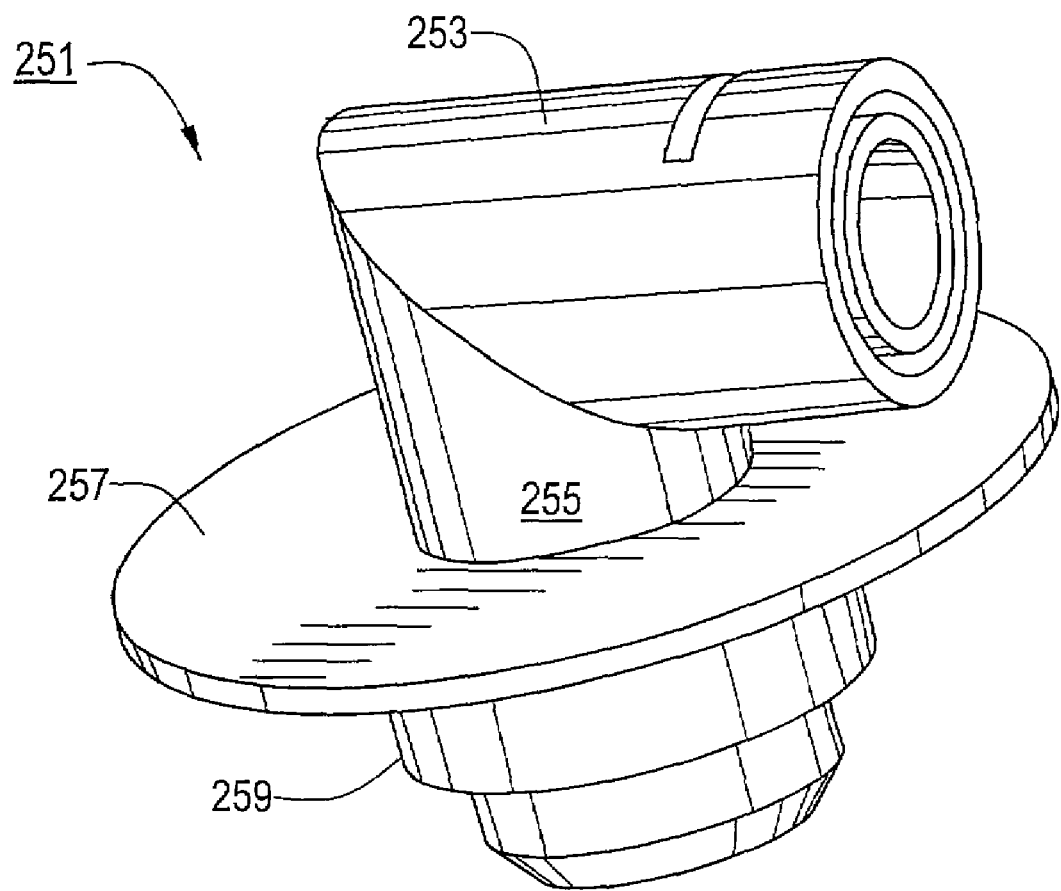
FIG. 12 is a perspective view of a fourth embodiment of a low profile adaptor constructed according to the teachings of the present invention for use with a gastrostomy feeding tube.

Referring now to FIG. 12, there is shown a perspective view of a fourth embodiment of a low profile adaptor constructed according to the teachings of the present invention for use with a gastrostomy feeding tube, said low profile adaptor being represented generally by reference numeral 251.

Adaptor 251 is similar in many respects to adaptor 11, one difference between the two adaptors being that adaptor 251 has an upper portion 253 that is generally cylindrical in shape, as opposed to being hourglass-shaped. Another difference is that adaptor 251 does not include a nut that serves as an external bolster. Instead, adaptor 251 has a lower portion 255 that is shaped to include an outwardly extending circumferential flange 257, flange 257 serving as an external bolster. Still another difference is that the bottom of lower portion 255 is shaped to include a circumferential ridge 259, ridge 259 being appropriately dimensioned so that the proximal end of a gastrostomy feeding tube may be inserted over ridge 259 and secured thereto by some securing mechanism, such as a ratchet-type clamp (not shown). In another embodiment (not shown), the bottom of lower portion 255 could simply be barb-shaped, with no additional mechanism being used to secure a gastrostomy feeding tube thereto.

Figure 13:
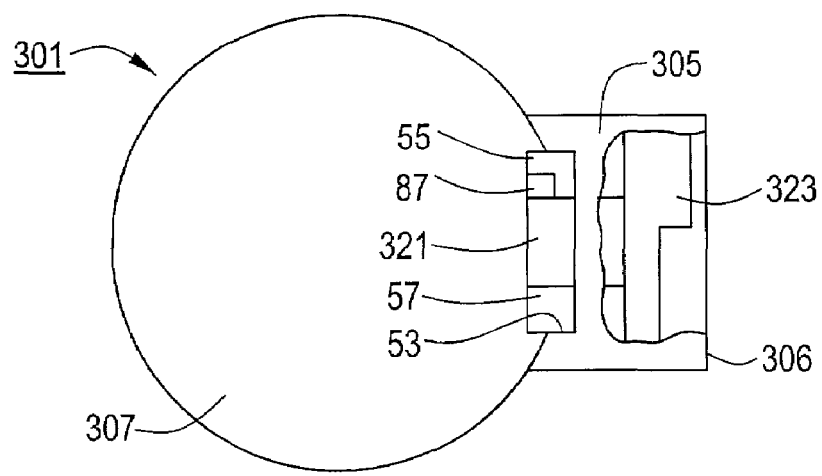
FIG. 13 is a top view, broken away in part, of a fifth embodiment of a low profile adaptor constructed according to the teachings of the present invention, said low profile adaptor being shown in its open position.
Figure 14:
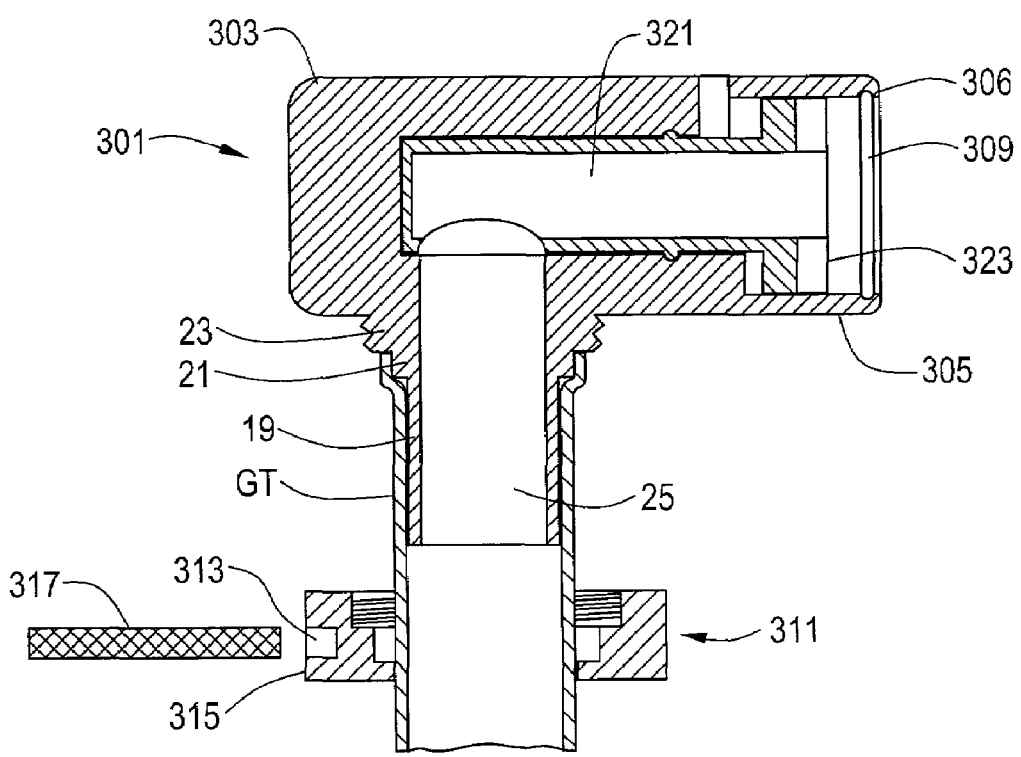
FIG. 14 a partially exploded section of the low profile adaptor of FIG. 13, said low profile adaptor being shown in its open position with a gastrostomy feeding tube inserted over a portion of the adaptor body.

Referring now to FIGS. 13 and 14, there are shown top and section views, respectively, of a fifth embodiment of a low profile adaptor constructed according to the teachings of the present invention for use with a gastrostomy feeding tube, said low profile adaptor being represented generally by reference numeral 301.

Adaptor 301 is similar in many respects to adaptor 11, one difference between the two adaptors being that, whereas adaptor 11 has a body 13 that is hourglass-shaped when viewed from above, adaptor 301 has a body 303 that, when viewed from above, includes a generally rectangular front portion 305 and a generally circular rear portion 307.

Another difference between the two adaptors is that the interior channel of front portion 305 is provided with a circular groove 309, the purpose of which will be discussed below.

Still another difference between the two adaptors is that adaptor 301 includes a nut 311, nut 311 being identical to nut 91, except that nut 311 is provided with a cylindrical cavity 313 extending radially inwardly from its outer surface 315 to a point prior to its inner bore. Adaptor 301 further includes a rod 317, rod 317 being insertable into cavity 313 to facilitate the tightening of nut 311 around a gastrostomy feeding tube and body 303.

Still yet another difference between the two adaptors is that adaptor 301 includes a stem 321, stem 321 being identical to stem 71, except that stem 321 has a front end 323 shaped to define a semi-annular tongue, instead of front end 73, which is provided with threads. Front end 323 is set back relative to front 306 of front portion 305.

Figure 15:
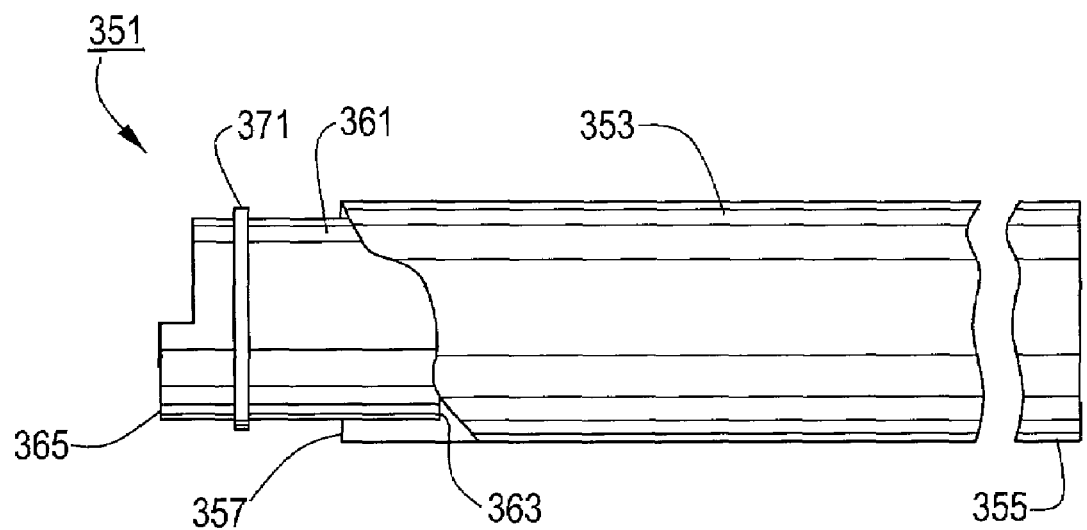
FIG. 15 is a side view, broken away in part, of a tube assembly suitable for use with the adaptor of FIG. 13.

Referring now to FIG. 15, there is shown a side view, broken away in part, of a tube assembly suitable for use with adaptor 301, said tube assembly being represented generally by reference numeral 351.

Figure 16:
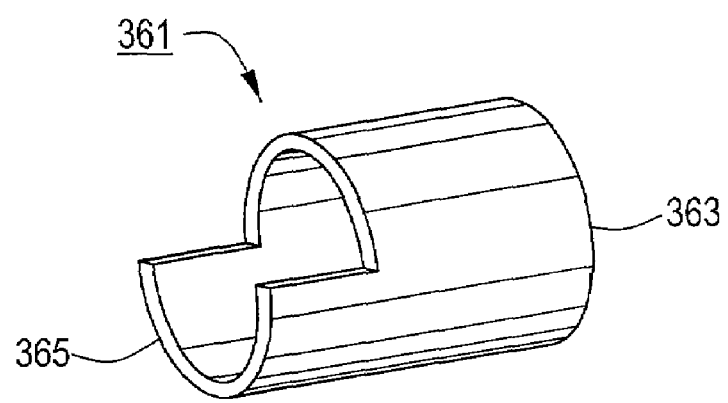
FIG. 16 is a perspective view of the connector shown in FIG. 15.

Assembly 351 includes a delivery tube 353 for use in conveying food and/or medications to a patient, delivery tube 353 having a proximal end 355 and a distal end 357. Assembly 351 also includes a hollow connector 361 (shown separately in FIG. 16), connector 361 having a proximal end 363 and a distal end 365. Proximal end 363 is inserted into distal end 357 of tube 353 and is retained therein by glue or a friction fit. Distal end 365 of connector 361 is shaped to define a semi-annular tongue dimensioned complemetarily to front end 323 of stem 321 so that distal end 365 of connector 361 can be fitted together with front end 323 of stem 321 and, thereafter, can be used to rotate stem 321. An O-ring 371 is securely mounted over connector 361, O-ring 371 being positioned on connector 361 so as to be received in groove 309 when connector 361 and stem 321 are fitted together. In this manner, engagement of connector 361 against stem 321 may be maintained.

As can readily be appreciated, the particular shapes of distal end 365 of connector 361 and front end 323 of stem 321 in the present embodiment are illustrative only; other mating or otherwise engageable arrangements for connector 361 and stem 321 could also be used.

As can also readily be appreciated, in addition to being used to administer food and/or medications to a patient, assembly 351 could alternatively be used for draining fluids from a patient.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. An adaptor well-suited for use with a medical catheter, said adaptor comprising:
   (a) a body, said body being provided with a first channel and a second channel, said first channel and said second channel being in fluid communication with one another, said first channel being adapted for fluid communication with the medical catheter, said second channel having a front end; and
   (b) a stem, said stem having a front, a rear, a side wall, a cavity extending rearwardly from said front end, and a hole in said side wall in fluid communication with said cavity, said stem being mounted within said second channel of said body with said front end of said stem being spaced rearwardly from said front end of said second channel, said stem being rotatable between an open position in which said stem and said first channel are in fluid communication with one another via said hole and a closed position in which said stem and said first channel are not in fluid communication with one another.

2. The adaptor as claimed in claim 1 wherein said body is shaped to include an upper portion and a lower portion, said upper portion being disposed on top of said lower portion.

3. The adaptor as claimed in claim 2 wherein said lower portion is generally cylindrical and is shaped to include a tube support, said tube support being insertable into the proximal end of the medical catheter, said tube support surrounding at least a portion of said first channel.

4. The adaptor as claimed in claim 3 wherein said second channel is disposed within said upper portion, said second channel being accessible from the front of said upper portion.

5. The adaptor as claimed in claim 4 wherein said first channel and said second channel are generally perpendicular to one another.

6. The adaptor as claimed in claim 3 further comprising means for securing the medical catheter to said lower portion.

7. The adaptor as claimed in claim 6 wherein said securing means comprises a ring-shaped member, said ring-shaped member being insertable over the medical catheter and said lower portion.

8. The adaptor as claimed in claim 7 wherein said ring-shaped member is provided with a recess extending radially inwardly from its outer surface, said adaptor further comprising a rod insertable into said recess.

9. The adaptor as claimed in claim 3 wherein said lower portion is further shaped to include at least one step of increasing outer diameter on top of said tube support.

10. The adaptor as claimed in claim 3 wherein said lower portion is further shaped to include lower and upper steps of increasing outer diameter on top of said tube support, said lower step being insertable into the proximal end of the medical catheter, said upper step being externally threaded.

11. The adaptor as claimed in claim 10 further comprising a nut insertable over the proximal end of the medical catheter and engageable with said upper step for securing the medical catheter to said lower portion, said nut having a bore complementarily shaped to said upper step, said lower step and at least a portion of said tube support.

12. The adaptor as claimed in claim 3 wherein said lower portion is shaped to include a tube support surrounding at least a portion of said first channel, said tube support being insertable into the proximal end of the medical catheter and having a barb at its bottom end.

13. The adaptor as claimed in claim 2 wherein said upper portion has a top surface, said top surface being hourglass-shaped.

14. The adaptor as claimed in claim 1 wherein less than the entirety of the periphery of said front end of said stem is shielded by said body.

15. The adaptor as claimed in claim 1 wherein the entire periphery of said front end of said stem is shielded by said body.

16. The adaptor as claimed in claim 1 wherein said front end of said stem is externally threaded to engage a complementarily threaded sleeve.

17. The adaptor as claimed in claim 16 wherein said front end of said stem is externally threaded to engage a complemetarily threaded sleeve surrounding a medical luer, said medical luer being insertable into said cavity of said stem.

18. The adaptor as claimed in claim 1 wherein said cavity of said stem is shaped to receive a medical luer.

19. The adaptor as claimed in claim 1 wherein the exterior of said side wall of said stem is shaped to include a stop block and wherein said second channel is shaped to include a pair of stop surfaces, said stop block being engageable with said stop surfaces in such a way as to limit the range of rotation of said stem between said open and closed positions.

20. The adaptor as claimed in claim 19 wherein said body is provided with a window to permit viewing of said stop block in said open and closed positions.

21. The adaptor as claimed in claim 20 wherein indicators are disposed on said body proximate to said window for correlating the position of said stop block with said open and closed positions.

22. The adaptor as claimed in claim 1 wherein the exterior of said side wall of said stem is shaped to include a snap seal and wherein said second channel is shaped to include a groove, said groove being shaped to receive said snap seal so as to keep said stem in place longitudinally within said second channel.

23. The adaptor as claimed in claim 1 wherein said rear of said stem is closed.

24. The adaptor as claimed in claim 1 wherein said rear of said stem is open.

25. The combination of an adaptor as claimed in claim 1 and a tube assembly, said tube assembly comprising a tube and a connector, said connector being hollow and having a proximal end and a distal end, said proximal end being coupled to said tube for fluid communication therewith, said distal end being matingly engageable with said front end of said stem for fluid communication therewith.

26. The combination as claimed in claim 25 wherein said distal end of said connector is shaped to define a semi-annular tongue, and wherein said front end of said stem is shaped to define a complementary semi-annular tongue.

27. The combination as claimed in claim 25 wherein said tube assembly further comprises an O-ring secured around said connector and wherein said second channel is shaped to include a groove, said groove being dimensioned to receive said O-ring to maintain engagement of said stem and said connector.

28. The combination of an adaptor as claimed in claim 1 and a syringe, said syringe having an inner cannula and an internally threaded outer sleeve at its distal end, said front end of said stem being externally threaded to engage said internally threaded outer sleeve and wherein said cavity of said stem is shaped to receive said inner cannula.

29. The combination as claimed in claim 28 wherein said inner cannula is a medical luer.

30. A PEG device comprising a gastrostomy feeding tube having a proximal end and a distal end, an internal bolster secured to the distal end of the gastrostomy feeding tube, and an adaptor as claimed in claim 1 secured to the proximal end of the gastrostomy feeding tube.

31. The combination of an adaptor as claimed in claim 1 and a drainage catheter, said drainage catheter being coupled to said body so as to be in fluid communication with said first channel.

* * * * *